United States Patent [19]

Vanderwerff

[11] 4,069,248
[45] Jan. 17, 1978

[54] HYDROLYSIS OF AROMATIC NITRILES TO CARBOXYLIC ACIDS

[75] Inventor: William D. Vanderwerff, West Chester, Pa.

[73] Assignee: Sun Oil Company of Pennsylvania, Philadelphia, Pa.

[21] Appl. No.: 747,152

[22] Filed: Dec. 3, 1976

Related U.S. Application Data

[63] Continuation-in-part of Ser. No. 602,613, Aug. 7, 1975, abandoned.

[51] Int. Cl.² ............................................. C07C 51/08
[52] U.S. Cl. ........................... 260/515 P; 260/515 R; 260/558 A
[58] Field of Search ................ 260/515 R, 515 P, 525

[56] References Cited

U.S. PATENT DOCUMENTS

| | | | |
|---|---|---|---|
| 2,734,080 | 2/1956 | Aroyan et al. | 260/515 P |
| 3,102,137 | 8/1963 | Wise et al. | 260/525 |
| 3,113,964 | 12/1963 | Farkas et al. | 260/515 P |
| 3,492,345 | 1/1970 | Neugebauer et al. | 260/515 P |
| 3,594,414 | 7/1971 | Katzschmann | 260/515 P |
| 3,873,610 | 3/1975 | Norton | 260/516 P |

Primary Examiner—James O. Thomas, Jr.
Assistant Examiner—James H. Reamer
Attorney, Agent, or Firm—J. Edward Hess; Donald R. Johnson; Paul Lipsitz

[57] ABSTRACT

In the non-catalytic hydrolysis to equilibrium of an aromatic nitrile, the improvement of carrying out such hydrolysis in the presence of a neutral salt whereby nitrogen impurities in the acid product are reduced.

6 Claims, No Drawings

HYDROLYSIS OF AROMATIC NITRILES TO CARBOXYLIC ACIDS

CROSS REFERENCE TO RELATED APPLICATION

This application is a continuation-in-part of Ser. No. 602,613, filed Aug. 7, 1975 and now abandoned.

It is known in the art to prepare aromatic carboxylic acids by hydrolysis of the corresponding nitriles which, in turn, are prepared by ammoxidation of alkyl-substituted hydrocarbons. The acids obtained from such processes must generally have high purity and be essentially devoid of nitrogen-containing by-products and, in the case of polycarboxylic acids, must also be free of any by-product mono-acids. This is particularly true of aromatic dicarboxylic acids such as terephthalic acid which is the well-known intermediate to polyester fibers. In order to employ terephthalic acid for such use it must have a very high purity and, in particular, be free of nitrogen containing bodies which will discolor the polymer made from such acid, and it must also be free of mono-acids since a mono-acid would adversely affect polymerization of the acid in that the necessary high molecular weight polymer could not be obtained.

It is also known in the art that nitrile hydrolysis may be carried out with an acid or an alkaline material as catalyst. For example, U.S. Pat. No. 2,979,526 discloses the use of ammonia, magnesia, sodium hydroxide, calcium carbonate and the like as suitable alkaline catalytic agents. Also, of interest is U.S. Pat. No. 3,381,034 which indicates that copper ions catalyze the hydrolysis and give hydrolysis products which are "relatively pure".

U.S. Pat. No. 2,734,080 is also of interest in that it relates to the recovery of phthalic acids in a manner to reduce the nitrogen content of the product. To achieve this the process of the reference employs a two or three stage hydrolysis of a mixture ammonium salts and amides of phthalic acids with a mineral acid as catalyst and in order to purify the filter cake slurries it with a bisulfate which may be made in situ from sodium sulfate and sulfuric acid, some sodium sulfate being in excess to help buffer the solution.

In the hydrolysis of aromatic nitriles to the corresponding carboxylic acids, as for example the hydrolysis of terephthalonitrile to terephthalic acid, there exists a chemical equilibrium between the intermediate amides and ammonium salts which may be illustrated as follows:

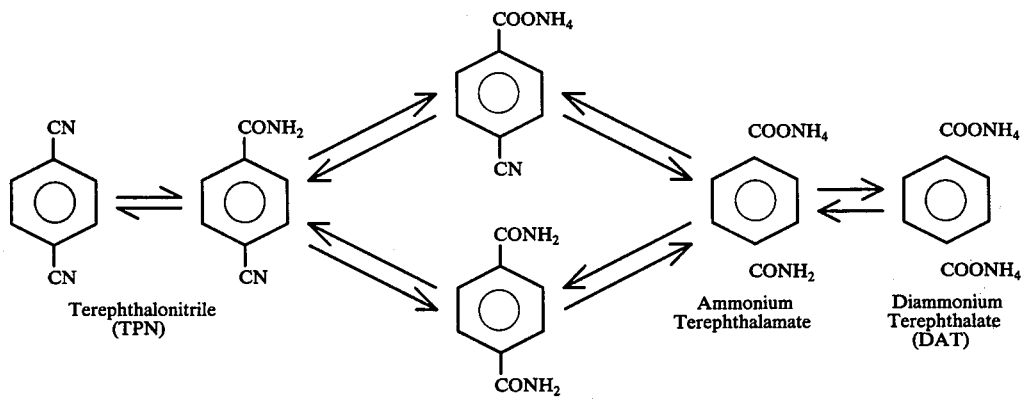

Terephthalonitrile (TPN) — Ammonium Terephthalamate — Diammonium Terephthalate (DAT)

Because of this equilibrium it is necessary to obtain high conversions to DAT in order to obtain product acid of acceptably high purity. Expressed another way, the amides present must be essentially completely converted to diammonium terephthalate so that all of the nitrogen may be removed as ammonia and no amide nitrogen remains in the product acid. This latter step of removing ammonia may be carried out by simply heating an aqueous solution of the diammonium salt, by steam distillation or by other techniques, but a very efficient means is by reactive distillation in the distillation reactor system disclosed in the copending application of Wynkoop and Hancock, Ser. No. 565,509, filed Apr. 7, 1975 now abandoned. When a nitrile hydrolysis reaction mixture is subjected to reactive distillation, a residence time is provided which enables conversion of the amide components to the diammonium salt as illustrated by the following equation:

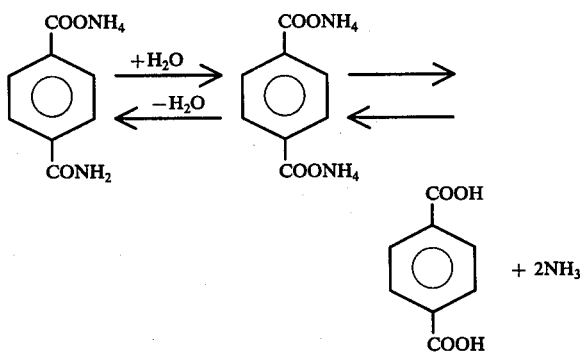

As can be seen, the equilibria are shifted to the right because of the continuous removal of ammonia from the reaction zone and, since all of the amide nitrogen eventually becomes converted to ammonia, a high purity free acid results as product. However, any means is desired by which the amide/salt equilibrium can be shifted to the right to obtain lower amide concentrations without adversely affecting other aspects of the process.

It has now been found that by increasing the ionic strength of the hydrolysis medium with a neutral, unreactive salt, the equilibrium can be shifted significantly to lower amide levels.

In carrying out the process of the invention the neutral salt will simply be added to the aqueous medium containing nitrile prior to conducting the hydrolysis, or alternatively, the salt may be added to the equilibrium mixture after hydrolysis and the mixture held on temperature for a time sufficient for the equilibrium shift to occur. Preferably, the salt will be added to the nitrile before hydrolysis and in general from about 0.5 to about 2.0 moles per liter of aqueous medium will be used.

As indicated, the salts employed in the process will be neutral and inert in the hydrolysis medium, that is, the salt must not alter the pH of the medium (as would a salt of a weak acid or weak base). Further the neutral salt must not be consumed or contribute to the reaction products (as would ammonium or terephthalate salts) and must not react with the intermediates or products of the hydrolysis (as certain heavy metals might). Also, the added salt must not be a source of corrosion (as chlorides might be to a titanium reactor). Salts which meet these criteria include the alkali metal sulfates, nitrates, phosphates, perchlorates and the like. Illustrative examples are sodium sulfate, potassium nitrate, sodium phosphate and lithium perchlorate. Preferred salts are sodium sulfate and trisodium phosphate.

The invention may be used in the hydrolysis of a wide variety of aromatic nitriles which will include the mono- and polynitriles of any aliphatic or aromatic compound. Preferably, mono- and dinitriles of the benzene and naphthalene series will be used and will include benzonitrile; tolunitrile; 1,4-dicyanobenzene; 1,3-dicyanobenzene; 2,6-dicyanonaphthalene; 1,8-dicyanonaphthalene and the like.

As indicated above, the nitrile hydrolysis is efficiently carried out by a reactive distillation and this invention may be used to advantage in such systems since the combined favorable effects of the salt addition of this invention with the distillation-reactor system makes for the production of acid with a low content of nitrogen impurities.

In order to further illustrate the process the following examples are given:

EXAMPLE I

A. To a two-liter all-titanium stirred autoclave is added 146.19 g. (0.88 moles) of terephthalic acid, 24.02 g. (0.12 moles) of diammonium terephthalate and 1000 ml. of water. This mixture is heated with stirring to 280° C and held at this temperature for approximately one hour. The resultant equilibrated mixture represents the hydrolyzate obtained by the non-catalytic hydrolysis of terephthalonitrile which would result from the removal, as ammonia, of 88 percent of the total available nitrogen from a one molal solution of terephthalonitrile. That this is so is clearly evident from the hydrolysis equilibria of a terephthalonitrile hydrolysis system which are discussed above. The reactor is then rapidly cooled to ambient temperature and sufficient NaOH is added to the contents of the reactor to effect complete solution at room temperature. An excess of $H_2SO_4$ is then added to effect precipitation of the terephthalic acid product. After filtration, thorough washing and drying, a sample of the acid is submitted for determination of parts per million (by weight) of nitrogen. The value of 2400 ppm corresponds to 2.84 mole percent terephthalamic acid.

B. The procedure of A is duplicated exactly except that the mixture charged to the autoclave is 146.19 g. (0.88 moles) of terephthalic acid. 24.02 g. (0.12 moles) of diammonium terephthalate, 142.05 g. (1.00 moles) of anhydrous sodium sulfate and 1000 ml. of water. The amide nitrogen content of the terephthalic acid product, determined as in example A, is 1300 ppm corresponding to 1.54 mole percent terephthalamic acid.

It is clear from these examples that the addition of the neutral salt resulted in a terephthalic acid product of significantly higher purity.

EXAMPLE II

Instead of adding the sodium sulfate to the synthetic hydrolysis mixture as in Example I, one mole of sodium sulfate is added to a one molal terephthalonitrile solution in an autoclave which is brought to 280° C for 1 hour to effect hydrolysis. After recovery of the terephthalic acid by precipitation with sulfuric acid as in Example I, it is found that the acid product has a lower nitrogen content than when no sodium sulfate is added to the hydrolysis reactor. Thus, the sodium sulfate has no adverse effect on the hydroysis system, but in fact contributes to a purity improvement.

The invention claimed is:

1. In the process of a non-catalytic aqueous equilibrium hydrolysis to the corresponding carboxylic acid of an aromatic nitrile obtained by ammoxidation of an alkyl-substituted hydrocarbon, the improvement which consists of increasing the ionic strength of the hydrolysis medium solution by adding to the nitrile prior to said hydrolysis an inert, neutral salt selected from the group of alkali metal sulfates, phosphates, and perchlorates in an amount from about 0.5 to about 2.0 moles per liter of aqueous medium whereby the content of nitrogen impurities in the acid product is reduced.

2. The process of claim 1 where the salt is sodium sulfate.

3. The process of claim 1 where the salt is trisodium phosphate.

4. The process of claim 1 where the aromatic nitrile is terephthalonitrile.

5. The process of claim 4 where the salt is sodium sulfate.

6. The process of claim 4 where the salt is trisodium phosphate.

* * * * *